United States Patent [19]

Bass

[11] Patent Number: 4,558,048

[45] Date of Patent: Dec. 10, 1985

[54] METHOD OF TREATING DIARRHOEA USING INDOLE COMPOUNDS

[75] Inventor: Robert J. Bass, Birchington, England

[73] Assignee: Pfizer Inc., New York, N.Y.

[21] Appl. No.: 716,773

[22] Filed: Mar. 27, 1985

[30] Foreign Application Priority Data

Apr. 6, 1984 [GB] United Kingdom ............... 8408913
Jan. 26, 1985 [GB] United Kingdom ............... 8501983

[51] Int. Cl.$^4$ ............... A61K 31/40; A61K 31/445; A61K 31/495; A61K 31/535
[52] U.S. Cl. ............... 514/232; 514/255; 514/323; 514/414; 514/418; 544/144; 544/373; 546/201; 548/467; 548/468; 548/484
[58] Field of Search ............... 544/144, 373; 546/201; 548/467, 468, 484; 514/232, 255, 323, 414, 418

[56] References Cited

U.S. PATENT DOCUMENTS 4,059,583 11/1977 McComsey et al. ............... 548/484

Primary Examiner—Robert W. Ramsuer

Attorney, Agent, or Firm—Charles J. Knuth; Peter C. Richardson; Mark Dryer

[57] ABSTRACT

Substituted phenylindoles, useful as anti-diarrhoeal agents and having the formula:

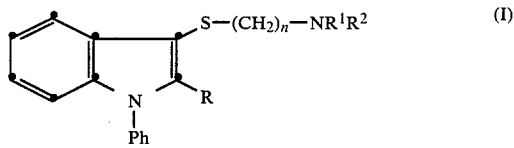

and the pharmaceutically-acceptable acid addition salts thereof;

wherein R is hydrogen, chloro, bromo, —CH(OH).Ph or —CH(OH).cyclohexyl; each Ph is phenyl or substituted phenyl; n is an integer of from 2 to 7; and each of $R^1$ and $R^2$ is hydrogen or ($C_1$-$C_4$) alkyl, or $R^1$ and $R^2$ taken together with the nitrogen atom to which they are attached form a heterocyclic group; and a method for the treatment of diarrhoea by the administration of said agents.

10 Claims, No Drawings

METHOD OF TREATING DIARRHOEA USING INDOLE COMPOUNDS

BACKGROUND OF THE INVENTION

This invention relates to therapeutic agents and, in particular, to 1-phenylindole derivatives which are valuable as antidiarrhoeal agents.

Diarrhoea is one of the major causes of morbidity and mortality in the world, and in developing countries it accounts for more infant fatalities than any other single cause. Even in North America and Europe it is a leading cause of death or debilitation among both the young and the elderly. Severe diarrhoea is most commonly caused by an infection of the small intestine; however, the microorganism itself does not invade the intestinal mucosa but produces an enterotoxin which is believed to be responsible for stimulating active electrolyte secretion and consequent fluid loss.

Although the introduction of oral hydration therapy has greatly simplified the treatment of dehydrating diarrhoea, drugs that reduce the rate of fluid loss also have an important role in the management of the condition. One such drug which has recently been identified as a promising antisecretory drug for use in the treatment of dehydrating diarrhoea is chlorpromazine. However, chlorpromazine also has marked effects on the central nervous system at the dosages used, most notably sedation. The present invention provides compounds which are useful in the treatment of diarrhoea but which are believed to have significantly reduced sedative effects.

SUMMARY OF THE INVENTION

In accordance with the invention there is provided a substituted phenylindole of the formula:

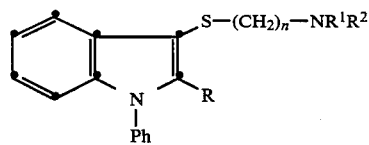

and the pharmaceutically-acceptable acid addition salts thereof;

wherein R is hydrogen, chloro, bromo, —CH(OH).Ph or —CH(OH).cyclohexyl; each Ph is phenyl or substituted phenyl; n is an integer of from 2 to 7; and each of $R^1$ and $R^2$ is hydrogen or ($C_1$–$C_4$) alkyl, or $R^1$ and $R^2$ taken together with the nitrogen atom to which they are attached form a heterocyclic group of the formula:

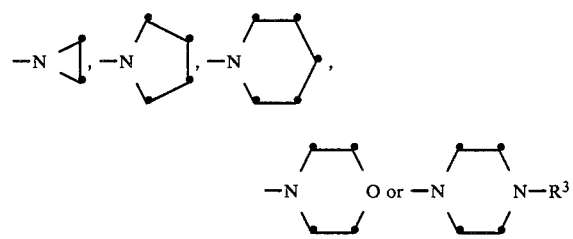

where $R^3$ is hydrogen or ($CH_1$–$C_4$) alkyl.

Each Ph is preferably either unsubstituted phenyl, or phenyl substituted with 1 to 3, more preferably 1 or 2, substituents selected from ($C_1$–$C_4$) alkyl, ($C_1$–$C_4$) alkoxy, F, Cl, Br, I and $CF_3$.

The invention further provides a method of treating diarrhoea in a patient, which comprises administering to said patient an effective amount of a compound of the formula (I) or a pharmaceutically-acceptable acid addition salt thereof.

Preferred compounds of the invention are those of formula (I) wherein R is hydrogen, chloro or bromo, more particularly wherein R is hydrogen.

"n" in one aspect is preferably 2, 3, 4 or 5, more preferably 2 or 3.

In another aspect "n" is 6 or 7, more preferably 6.

Each of $R^1$ and $R^2$ is hydrogen or ($C_1$–$C_4$) alkyl, more preferably hydrogen or methyl. Most preferably each of $R^1$ and $R^2$ is methyl.

"Ph" is preferably unsubstituted phenyl.

In the preferred individual compound, R is hydrogen $R^1$ and $R^2$ are methyl, n is 6 and Ph is unsubstituted phenyl.

DESCRIPTION OF THE INVENTION

The compounds of the formula (I) in which R is hydrogen may be prepared by reacting a salt of the formula:

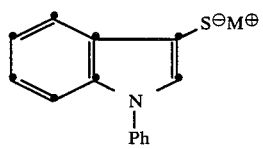

where Ph is as previously defined and $M^+$ is an alkali metal or alkaline earth metal cation, with a compound of the formula:

$$Q.(CH_2)_n.NR^1R^2 \quad (III)$$

or an acid addition salt thereof, where n, $R^1$ and $R^2$ are as defined above and Q is a leaving group, e.g. chloro, bromo, tosyloxy, etc.

Q is preferably chloro. M is preferably an alkali metal, most preferably sodium or potassium.

The compounds of the formula (II) are preferably generated in situ by the reaction of a compound of the formula:

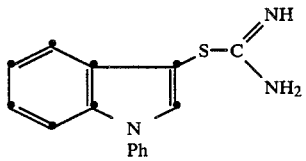

or an acid addition salt thereof, with an alkali metal hydroxide or alkaline earth metal hydroxide such as sodium hydroxide or potassium hydroxide.

Some of the compounds of the formula (III) are unstable in their free base forms, and in these cases they should be used in acid addition salt form (eg as hydrochlorides). Such compounds are in fact often commercially available as hydrochlorides.

Thus a typical reaction involves the reaction of compound (IV), optionally in acid addition salt form such as a hydroiodide, with aqueous sodium hydroxide, preferably with heating at up to reflux. Excess sodium hydroxide should be used if compound (IV) is used in acid addition salt form. After stirring for a short period, compound (III) is added to the suspension, if necessary in acid addition salt form. The resulting reaction is generally exothermic. The product can then be isolated and purified conventionally. In some cases, the product can be isolated directly in acid addition salt form.

The starting materials (IV) can be obtained conventionally, e.g. as follows:

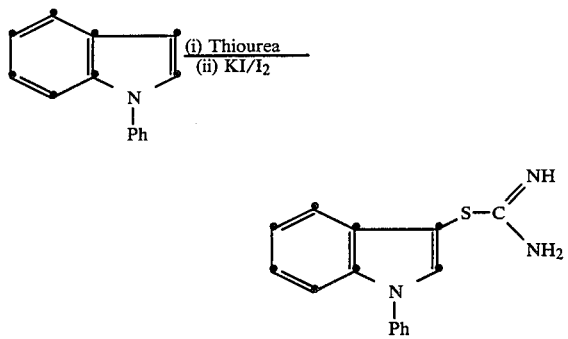

(usually as the hydroiodide salt).

If desired, acid addition salts may be prepared from the free base forms by reaction of a solution of the free base in a suitable organic solvent, e.g. dry methanol, with a solution of the desired acid in a suitable organic solvent, e.g. dry methanol, and either evaporating the solvent or recovering the salt as a precipitate.

In an alternative to the above, the compounds (II) can be reacted as follows to prepare the end products of the formula (I):

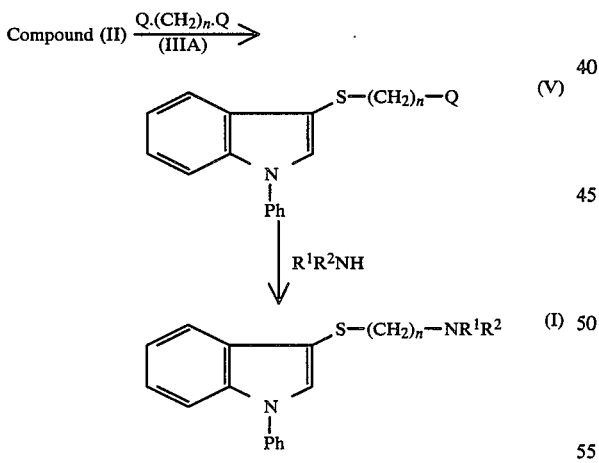

$R^1$, $R^2$, Q and n are as defined for formula (I); Q is preferably Br in this alternative.

Again it is preferred to generate the compound (II) in situ by reacting the compound (IV) with aqueous sodium hydroxide at up to the reflux temperature, e.g. 90° C. The compound (IIIA) is then added in a suitable organic solvent, e.g. ethanol, and the reaction mixture heated at up to the reflux temperature for a few hours. The crude intermediate (V) is then recovered from the reaction mixture and reacted with the compound $R^1R^2NH$ in a suitable organic solvent, e.g. tetrahydrofuran, and generally at low temperature, typically 0° to 10° C. The product (I) can then be isolated and purified conventionally.

The compound (IV) can again be reacted in acid addition salt form and in this case, as before, excess sodium hydroxide should be used.

Compounds in which R is —CH(OH).Ph or —CH(OH).cyclohexyl can be prepared from the corresponding compounds (or their acid addition salts) in which R is H, firstly by reaction with a strong base such as n-butyllithium and then with, respectively, the appropriate benzaldehyde or cyclohexane carboxaldehyde. Typically the reaction with n-butyllithium is carried out at low temperature, e.g. −40° C., in an organic solvent, such as tetrahydrofuran. The reaction mixture is then maintained at low temperature, e.g. −25° C., for a few hours, and then cooled to about −70° C. before the dropwise addition of the aldehyde in e.g. tetrahydrofuran. The reaction mixture is then slowly allowed to warm to room temperature and evaporated. The desired product can be recovered from the residue and purified by conventional techniques.

Compounds in which R is Cl or Br can be prepared by a 2-stage reaction from the corresponding compounds in which R is H, as follows:

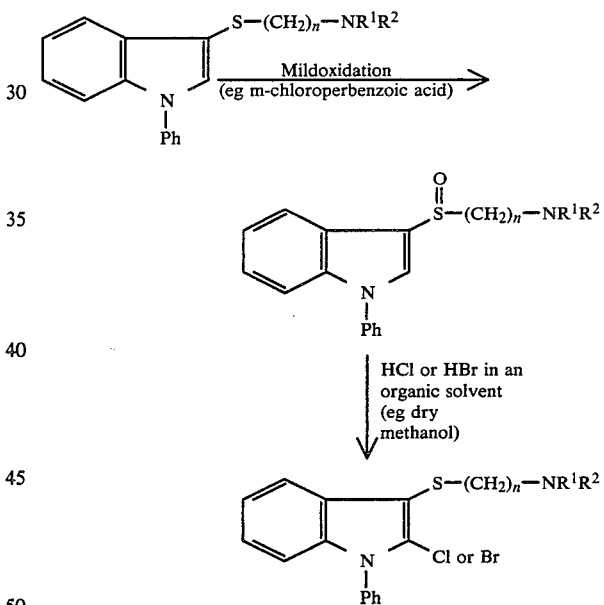

The reaction can be carried out conventionally (see Example 4).

Acids from which pharmaceutically acceptable addition salts of the compounds of the invention can be prepared are those which form non-toxic addition salts containing pharmaceutically acceptable anions, such as the hydrochloride, hydrobromide, hydroiodide, sulphate or bisulphate, phosphate or acid phosphate, acetate, maleate, fumarate, lactate, tartrate, citrate, gluconate, saccharate and p-toluene sulphonate salts.

The compounds of the invention are valuable for the treatment of diarrhoea in both humans and animals, especially for the treatment of severe forms of diarrhoea of bacterial origin, for example, associated with *E. coli* infections in humans and enteritis in pigs. The compounds are also of value in treating milder forms of the condition such as travellers' diarrhoea.

The activity of the compounds is assessed using a test procedure based on that described by Giannella in Infection and Immunity 1976, 14, 95–99, in which the ability of the compounds to inhibit the intestinal secretion induced by administration of an enterotoxin is measured in suckling mice. In practice a group of mice are given an oral dose of a heat stable toxin produced by *E. coli* as described by Staples et. al., J. Biol. Chem., 1980, 255, 4716. This induces intestinal fluid secretion and causes an increase in gut weight relative to that of the remaining carcass. A further group of mice are dosed with the toxin followed by the compound under investigation at various dose levels. After 2½ hours at 23° C. the mice are killed and the weight of the gut measured as a proportion of the remaining carcass. The percentage inhibition at various dose levels is then calculated. The test can also be performed using a heat labile enterotoxin, produced for example by *Vibrio cholerae* as described by Kusama and Craig, Infection and Immunity, 1970, 1, 80.

For human use, the anti-diarrhoeal compounds of the formula (I) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic.

For oral administration to human patients, the daily dosage level of the anti-diarrhoeal compounds of the formula (I) will be from 1–40 mg./kg., preferably 5–10 mg./kg. (in divided doses). Thus tablets or capsules of the compounds can be expected to contain from 5 mg to 25 mg of active compound for administration singly or two or more at a time as appropriate. In any event the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

The preparation of the compounds of the formula (I) is illustrated by the following Examples. All temperatures are in °C.:

EXAMPLE 1

(A) 2-(1-phenylindol-3-yl)-2-thioisourea hydroiodide

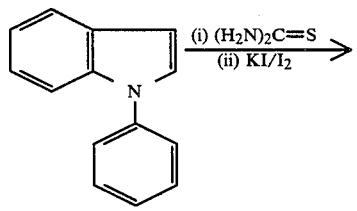

-continued

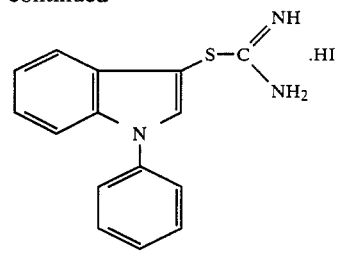

N-Phenylindole (28.95 g; 0.15M) and thiourea (11.4 g; 0.15M) were dissolved in a mixture of methanol (140 ml) and ethanol (100 ml) by rapid stirring at 20°. To this solution was added in four portions a solution of potassium iodide (52.5 g; 0.3M) and iodine (38.1 g; 0.15M) in water (60 ml) over 10 minutes. The solution was then stirred at 20° for 17 hours. The resulting heavy yellow precipitate of the crude product was filtered off, washed successively with isopropanol (3×200 ml), water (3×200 ml), isopropanol (3×200 ml) and ether (2×200 ml), and then dried at 60° to give the title compound, weight 46.2 g (78.0% yield). An analytical sample was prepared by crystallisation from a 1:1 mixture of methanol and ethanol. This gave colourless rhombohedral crystals of the title compound, m.p. 264°–6°.

Analysis %: Calculated for $C_{15}H_{13}N_3S.HI$: C,45.5; H,3.5; N,10.6; Found: C,45.1; H,3.4; N,10.1.

N.m.r. and i.r. were constistent with the stated structure.

(B)
3-(3-[N,N-Dimethylamino]propylthio)-1-phenylindole hydrochloride

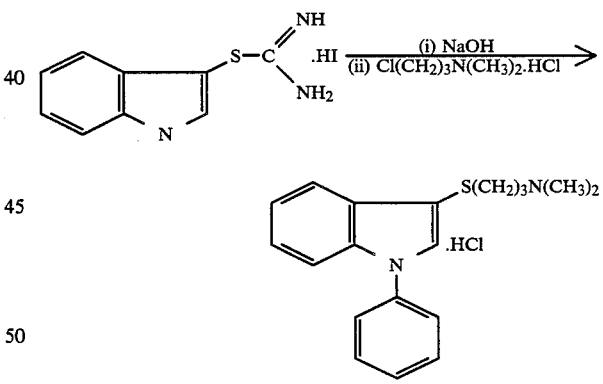

A suspension of the hydroidide salt from part (A) (27.0 g; 0.07M) in 2N aqueous sodium hydroxide (300.0 ml) was stirred under nitrogen and heated to reflux. After 10 minutes the mixture was cooled to 90° and solid 3-[dimethylamino]-propyl chloride hydrochloride (21.6 g; 0.14M) was added in small portions. A vigorous exothermic reaction occcurred and the solid dissolved. The solution was allowed to cool and was stirred at 20° for a further 17 hours. The resulting two-phase mixture was extracted with methylene chloride (3×100 ml.), and the combined organic extracts were washed with water (2×50 ml), dried (magnesium sulphate) and evaporated to give a viscous pale green oil. This was dissolved in 3.5N methanolic hydrogen chloride (50 ml.), evaporated and the residue was crystallised from acetonitrile (1200 ml.) to give the title compound as colourless leaflets, weight 11.3 g, m.p. 203°-7° (46.0% yield).

Analysis %: Calculated for $C_{19}H_{22}N_2S.HCl$: C,65.8;H,6.7;N,8.1; Found: C,65.6;H,6.8;N,8.0.

EXAMPLES 2 and 3

The following compounds were prepared similarly to Example 1(B), starting from the same hydroiodide salt and, respectively, $Cl(CH_2)_3NH_2.HCl$ and $Cl(CH_2)_2N(CH_3)_2.HCl$:

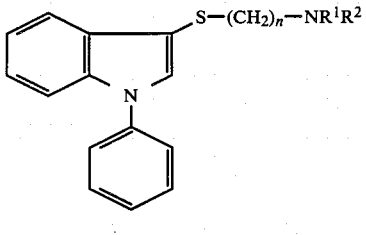

| EX-AM-PLE NO. | n | R¹ | R² | Form Isolated | m.p. (°C.) | Analysis % (Theoretical in brackets) | | |
|---|---|---|---|---|---|---|---|---|
| | | | | | | C | H | N |
| 2 | 3 | H | H | Hydrochloride hemihydrate | 139–40° | 62.6 (62.3 | 6.0 6.1 | 8.7 8.5) |
| 3 | 2 | CH₃ | CH₃ | Hydrochloride | 178–183° | 64.5 (64.9 | 6.3 6.4 | 8.3 8.4) |

The product of Example 2 was crystallised from isopropanol (94% yield). The product of Example 3 was crystallised from isopropanol/dry ethyl acetate (36.2% yield).

EXAMPLE 4

(A)

3-(3-[N,N-dimethylamino]propylsulphinyl)-1-phenylindole, free base and maleate

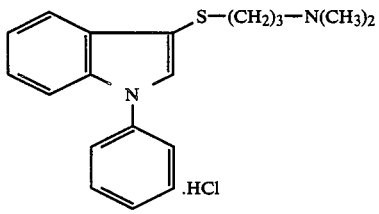

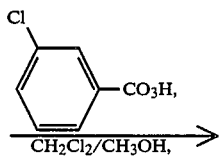

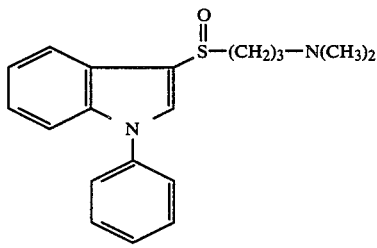

A solution of m-chloroperbenzoic acid (3.1 g; 0.018M) in dry methylene chloride (50 ml) was added dropwise to a stirred solution of 3-(3-[N,N-dimethylamino]propylthio)-1-phenylindole hydrochloride (5.20 g; 0.015M) in a mixture of dry methylene chloride (125 ml) and dry methanol (3 ml) at 20°. After 17 hours, the solution was washed with 5% aqueous sodium carbonate (250 ml), dried (magnesium sulphate) and evaporated. The residual oil was purified by chromatography under slight excess pressure (0.2 kg.cm.²) on a 200 g. Merck "Kieselgel 60" (Trade Mark) (230–400 mesh) silica-packed column (diameter 75 mm.) eluting with ethyl acetate/diethylamine firstly in a ratio of 98:2 v/v (1 liter), then 95:5 v/v (1 liter) and then 90:10 v/v until the product was eluted. The product-containing fractions were combined and evaporated to give the free base form of the title compound, weight 3.5 g (71.5% yield). A solution of maleic acid (96 mg; 0.00082M) in dry methanol (2 ml.) was added to a solution of said free base (270 mg; 0.00082M) in dry methanol (10 ml) and the solvent was evaporated. The residue was crystallised from dry ethyl acetate to give the title compound, maleate salt, weight 248 mg, m.p. 116°-9° (73.8% yield).

Analysis %: Calculated for $C_{19}H_{22}N_2OS.C_4H_4O_4$: C,62.4; H, 5.9; N,6.3; Found: C,62.2; H,5.8; N,6.5.

N.m.r, i.r. and mass spectral data were consistent with the stated structure.

(B)

2-Chloro-3-(3-[N,N-dimethylamino]propylthio)-1-phenylindole, free base and hydrochloride

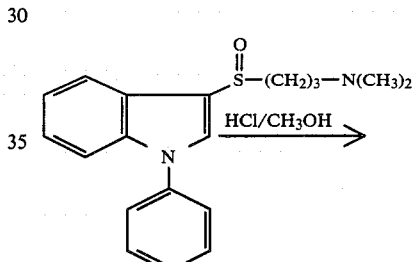

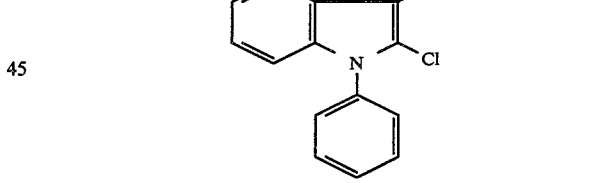

4.4N Methanolic hydrogen chloride (8 ml) was added to a solution of the free base of 3-(3-[N,N-dimethylamino]propylsulphinyl)-1-phenylindole (3.5 g; 0.0107M) in dry methanol (40 ml) and the solvent was evaporated. Further 4.4N methanolic hydrogen chloride (8 ml) was added to the residue and the solvent was again evaporated. The residue was dissolved in methylene chloride (400 ml), washed with 5% aqueous sodium carbonate (400 ml), dried (magnesium sulphate) and evaporated. The residual oil was purified by chromatography under slight excess pressure (0.2 kg cm²) on a 60 g. Merck "Kieselgel 60" (Trade Mark) (230–400 mesh) silica-packed column (diameter 50 mm) eluting with ethyl acetate/isopropanol/0.88 S.G. NH₄OH firstly in a ratio of 98:2:1.5 v/v/v (400 ml.), then 96:4:3 v/v/v (400 ml.) and finally 94:6:4.5 until the product was eluted. The product-containing fractions were combined and evaporated to give the free base form of the title compound, weight 2.14 g. (57.8% yield). 4.4N Methanolic hydrogen chloride (3 ml) was added to a solution of said free base (200 mg; 0.00058M) in dry methanol (10 ml) and the solvent was then evaporated. The residue was crystallised from dry ethyl acetate to give the title compound as a hydrochloride weight 171 mg, m.p. 171°-6° (77.3% yield).

Analysis %: Calculated for $C_{19}H_{21}ClN_2S.HCl$: C,59.8; H,5.8; N,7.3; Found: C,60.0; H,5.9; N,7.6.

N.m.r., i.r. and mass spectral data were consistent with the stated structure.

EXAMPLE 5

1-Phenyl-3-[6-(N,N-dimethylamino)-n-hexylthio]indole citrate

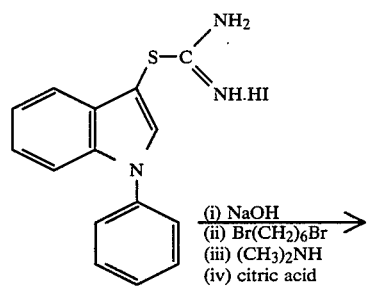

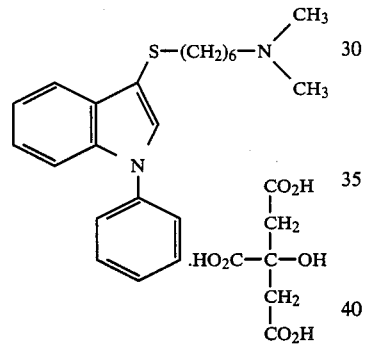

1-Phenylindole-3-isothiuronium iodide (5 g; 12.65 mMole) was heated at 90° with stirring under nitrogen in 2N aqueous sodium hydroxide for 25 minutes. On cooling to room temperature, 1,6-dibromohexane (12.2 g; 0.05 mole) was added in absolute ethanol (50 ml) and the reactants were vigorously stirred under reflux for 5 hours. The aqueous layer was separated from the resultant two-phase mixture and extracted with ether (2×50 ml). The combined organic layer and organic extracts were washed with water (100 ml), dried (magnesium sulphate) and evaporated. The excess 1,6-dibromohexane was removed by distillation (115°/10 mmHg) and the residual tar was dissolved in anhydrous tetrahydrofuran (30 ml). To the stirred solution at 0° was added anhydrous dimethylamine (5 ml; 0.075 mole) and the reactants were stirred at 5°±5° for 1 hour and then at room temperature for 15 hours. The solution was filtered, the filtrate evaporated and the residue partitioned between methylene chloride (30 ml) and water (30 ml). The aqueous layer was separated and further extracted with methylene chloride (2×30 ml). The combined organic layer and organic extracts were washed with brine, dried (magnesium sulphate) and evaporated. The residual oil was purified by medium pressure chromatography (0.14 Kg cm$^{-2}$) on a 30 g. Merck "Kieselgel 60" (230-400 mesh) (Trade Mark) silica-packed column (diameter 40 mm), eluting with chloroform/methanol/0.88 ammonia, firstly in the ratio of 98:2:0.2 v/v (200 ml) and then 90:10:1 (200 ml). Fractions containing the product as the major component (as evidenced by thin layer chromatographic analysis) were evaporated to give an oil (2 g). 1.05 g of this oil was dissolved in sodium-dried ether (5 ml) and a solution of citric acid hydrate (0.625 g; 3.25 mMole) in methanol (2 ml) was added. The ensuing solid was triturated with sodium-dried ether (10 ml), filtered and the solid product recrystallised from acetone/ether and vacuum-dried at 70° for 15 hours to give the title compound, weight 1.33 g, m.p. 86-88°, (35% yield).

Analysis %: Found: C,61.8; H,6.8; N,5.1; Calculated for $C_{22}H_{28}N_2S.C_6H_8O_7$: C,61.7; H,6.7; N,5.1.

N.M.R. and i.r. spectral data were consistent with the stated structure.

EXAMPLE 6

1-Phenyl-2-(1-phenyl-hydroxymethyl)-3-(3-N,N-dimethylaminopropylthio)indole oxalate

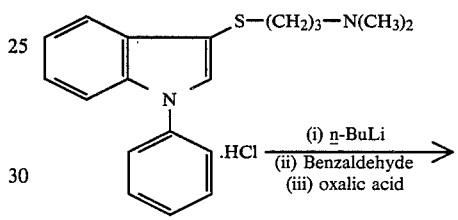

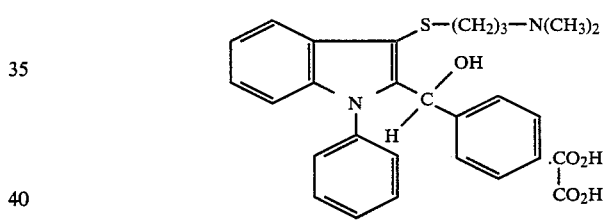

A solution of n-butyllithium in hexane (12.5 ml of a 1.6M solution; 20 mMole) was added dropwise to a stirred suspension of the hydrochloride of 1-phenyl-3-(3-N,N-dimethylaminopropylthio)indole (1.04 g; 3 mMole) in dry tetrahydrofuran (40 ml) at −40° in an atmosphere of nitrogen. The solution obtained was maintained at −25° for 3 hours, cooled to −70° and a solution of benzaldehyde, (4.3 g; 40 mMole) in dry tetrahydrofuran (10 ml) was added dropwise. The solution was allowed to warm up to +20° over a period of 17 hours and then evaporated. The residue was dissolved in a mixture of 0.5N hydrochloric acid (200 ml) and methylene chloride (200 ml) which was basified to pH 10 by addition of solid sodium carbonate. The resulting separated aqueous layer was extracted with methylene chloride (2×100 ml) and the combined organic layer and organic extracts were dried (magnesium sulphate) and evaporated. The residual oil was purified by medium pressure chromatography (0.2 Kgcm$^{-2}$) on a 60 g Merck "Kieselgel 60" (230-400 mesh) silica-packed column (diameter 50 mm) eluting with ethyl acetate/propan-2-ol/concentrated aqueous ammonia firstly in the ratio 98:2:0.5 (500 ml), then 97:3:2 (500 ml) and then 96:4:2.5 (500 ml). The appropriate fractions were combined and evaporated and the residual oil (743 mg; 1.77 mMole) was dissolved in methanol (10 ml). A solution of anhydrous oxalic acid (160 mg; 1.77 mMole) in methanol (2 ml) was added, the solution evaporated and the residue crystallised from ethyl acetate/cyclohexane to give the title compound, weight 783 mg; m.p. 160°-4°, (51.6% yield).

Analysis: Found: C,66.1; H,6.0; N, 5.4; Calculated for $C_{26}H_{28}N_2OS \cdot C_2H_2O_4$: C,66.4; H,6.0; N,5.5.

N.M.R., i.r. and mass spectral data were consistent with the stated structure.

EXAMPLE 7

1-Phenyl-2-(1-cyclohexyl-hydroxymethyl)-3-(3-N,N-dimethylaminopropylthio)indole oxalate

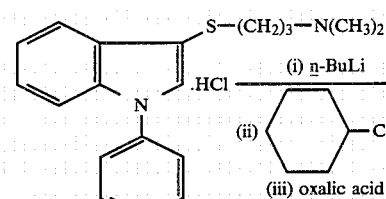

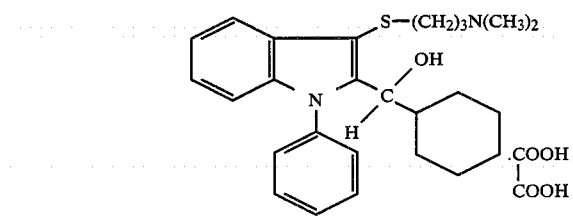

A solution of n-butyllithium in hexane (7.5 ml of a 1.6M solution; 12 mMole) was added dropwise to a stirred suspension of the hydrochloride of 1-phenyl-2-(3-N,N-dimethylaminopropylthio)indole (693 mg; 2 mMole) in dry tetrahydrofuran (20 ml) at −40° in an atmosphere of nitrogen. The solution obtained was maintained at −25° for 3 hours, cooled to −70° and a solution of cyclohexane carboxaldehyde (2.8 g; 25 mMole) in dry tetrahydrofuran (5 ml) was added dropwise. The solution was allowed to warm up to +20° over a period of 17 hours and then evaporated. The residue was dissolved in a mixture of 0.5N hydrochloric acid (50 ml) and methylene chloride (50 ml) which was basified to pH 10 by addition of solid sodium carbonate. The resulting separated aqueous layer was extracted with methylene chloride (2×50 ml) and the combined organic layer and extracts were dried (magnesium sulphate) and evaporated. The residual oil was purified by medium pressure chromatograpy (0.2 kg cm$^{-2}$) on a 50 g Merck "Kieselgel 60" (230–400 mesh) silica-packed column (diameter 50 mm) eluting with ethyl acetate/propan-2-ol/concentrated aqueous ammonia firstly in the ratio 98:2:0.5 (500 ml), then 97:3:1 (500 ml) and then 96:4:1.5 (500 ml). The appropriate fractions were combined and evaporated and the residual oil (480 mg; 1.14 mMole) was dissolved in methanol (10 ml). A solution of anhydrous oxalic acid (102 mg; 1.14 mMole) in methanol (2 ml) was added, the solution evaporated and the residue crystallised from ethyl acetate to give the title compound, weight 458 m.p. 138°–143°, (44.7% yield).

Analysis %: Found: C,65.5; H,7.4; N,5.4; Calculated for $C_{26}H_{34}N_2OS \cdot C_2H_2O_4$: C,65.6; H,7.1; N,5.5.

N.M.R., i.r. and mass spectral data were consistent with the stated structure.

I claim:

1. A method for the treatment of diarrhoea in a patient, which comprises administering to said patient an effective amount of a substituted phenylindole of the formula:

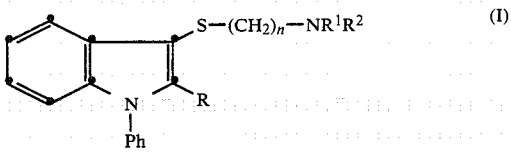

or a pharmaceutically-acceptable acid addition salt thereof;

wherein R is hydrogen, chloro, bromo, —CH(OH).Ph or —CH(OH).cyclohexyl; each Ph is phenyl or substituted phenyl; n is an integer of from 2 to 7; and each of $R^1$ and $R^2$ is hydrogen or ($C_1$–$C_4$) alkyl, or $R^1$ and $R^2$ taken together with the nitrogen atom to which they are attached form heterocyclic group of the formula:

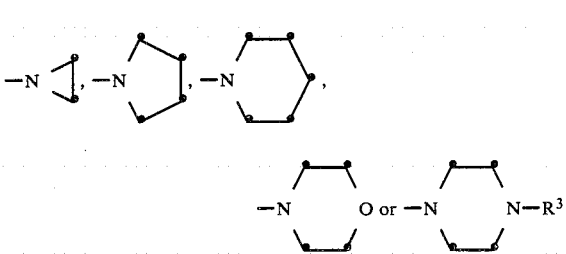

where $R^3$ is hydrogen or ($C_1$–$C_4$) alkyl.

2. A method according to claim 1, in which, in the compound of formula (I), each Ph is unsubstituted phenyl, or phenyl substituted with 1 to 3 substituents selected from ($C_1$–$C_4$) alkyl, ($C_1$–$C_4$) alkoxy, F, Cl, Br, I and $CF_3$.

3. A method according to claim 2, in which each Ph is unsubstituted phenyl.

4. A method according to claim 1, in which, in the compound of formula (I), R is hydrogen, chloro, —CH(OH).phenyl or —CH(OH).cyclohexyl.

5. A method according to claim 4, in which R is hydrogen.

6. A method according to claim 1, in which, in the compound of formula (I), each of $R^1$ and $R^2$ is hydrogen or methyl.

7. A method according to claim 1, in which, in the compound of formula (I), n is 2, 3 or 6.

8. A method according to claim 1, in which, in the compound of formula (I), R is hydrogen, chloro, —CH(OH).phenyl or —CH(OH).cyclohexyl; each of $R^1$ and $R^2$ is hydrogen or methyl; Ph is unsubstituted phenyl; and n is 2, 3 or 6.

9. A method according to claim 1, in which the compound of formula (I) is the compound wherein R is hydrogen, each of $R^1$ and $R^2$ is methyl, n is 6 and Ph is unsubstituted phenyl.

10. A method according to claim 1, in which, in the compound of formula (I), n is an integer of from 2 to 5, R is hydrogen, chloro or bromo, and Ph, $R^1$ and $R^2$ are as defined in claim 1.

* * * * *